US00PP10610P

United States Patent [19]

Swartz et al.

[11] Patent Number: Plant 10,610

[45] Date of Patent: Sep. 22, 1998

[54] RASPBERRY PLANT NAMED 'LAUREN'

[76] Inventors: Harry Jan Swartz, 16022 Jerald Rd., Laurel, Md. 20707; Joseph A. Fiola, 1400 Paterson Ave., Whiting, N.J. 08759; Herbert D. Stiles, 811 Brunswick Ave., Blackstone, Va. 23824; Brian A. Smith, 311 N. Dallas St., River Falls, Wis. 54022

[21] Appl. No.: 630,180

[22] Filed: Apr. 10, 1996

[51] Int. Cl.[6] ..... A01H 5/00

[52] U.S. Cl. ..... Plt./46.2

[58] Field of Search ..... Plt./46.2

[56] References Cited

U.S. PATENT DOCUMENTS

P.P. 6,493 12/1988 Wilhelm ..... Plt./46.2

P.P. 7,437 2/1991 Ackerman ..... Plt./46.2

*Primary Examiner*—James R. Feyrer

*Attorney, Agent, or Firm*—Marian P. Marks; Sana A. Pratt

[57] ABSTRACT

This invention relates to a new and distinct spring bearing red raspberry cultivar named 'Lauren' which is capable of producing large fruit of floricanes that ripen 1 to 3 weeks earlier than 'Titan', the only other large fruited cultivar grown in the eastern United States, and several days to weeks earlier than most standard cultivars currently in widespread use. The cultivar is characterized by its moderate suckering ability, its conic, smooth and symmetrical fruit. Additionally, its canes are upright and vigorous, and it does not normally produce a fall crop.

3 Drawing Sheets

ORIGIN OF THE NEW CULTIVAR

The new cultivar of spring bearing red raspberry originated from a controlled cross at the University of Maryland Greenhouses in College Park, Md. The cross, "DH", was 'Southland'×'Titan' and was made in winter of 1982. This year was designated "C", as part of the University of Maryland at College Park; Rutgers University of New Brunswick, N.J.; Virginia Polytechnic Institute and State University, Southern Piedmont Agricultural Research and Education Center at Blackstone; and the University of Wisconsin at River Falls cooperative breeding program. The clone was the first of the progeny selected in 1985 at the Wye Research and Education Center site near Queenstown, Md. and was therefore designated "–1". Thus the complete breeding designation was "CDH-1".

The new cultivar has been reproduced asexually by tissue culture techniques at Nourse Berry Farm, 41 River Road, South Deerfield, Mass. 01373, and tested in evaluation fields first by the cooperating breeders, and then by licensed evaluators. Through the several thousand plants produced by tissue culture and standard asexually reproduced plants from root suckers, no off-type phenotype plants have been noted. The seedling clone "CDH-1" has been designated cultivar 'Lauren' upon agreement of all cooperators and representatives.

SUMMARY OF THE NEW CULTIVAR

This application relates to a new and distinct spring bearing red raspberry cultivar, botanically known as *Rubus ideaus* L.. The following characteristics are outstanding and warrant this process.

1. Production of large fruit on floricanes that ripen 1 to 3 weeks earlier than 'Titan', the only other large fruited cultivar grown in the eastern U.S., and several days to a week earlier than most standard cultivars currently in widespread use.

2. In warmer climates, fruit is as large, more flavorful and more cohesive (does not crumble) than fruit of 'Titan', and firmer and larger than fruit of 'Southland', both widely grown cultivars and the parents of CDH-1.

The following characteristics are distinguishing and can be useful for cultivar identification.

1. Fruit of CDH-1 is very large, averaging up to 4.2 g fruit in warm climates. The only cultivar matching this size is 'Titan', which ripens several days to weeks after CDH-1.

2. Plants are moderately suckering, but slightly more so than 'Titan', producing half to 75% as many canes as 'Southland', one of its parents.

3. Fruit is truncated conic, smooth and symmetrical, more cohesive than 'Titan', but less so than others. The fruit does not normally sunscald but will in certain years produce double receptacle fruit that resemble the shape of a hawk's bill.

4. Fruit has a slightly uneven collar.

5. Canes are upright and vigorous, more so than most cultivars in use in the eastern U.S. but less vigorous than 'Latham'. The plant is only moderately susceptible to root rot caused by *Phytophthora fragarae*.

6. The canes do not normally produce a fall crop, as does 'Southland', one of its parents, or 'Titan', which may produce a late fall crop on occasion in warmer climates.

BRIEF DESCRIPTION OF THE PHOTOGRAPHS

The accompanying photographs show typical characteristics of the new variety:

Figure 4:
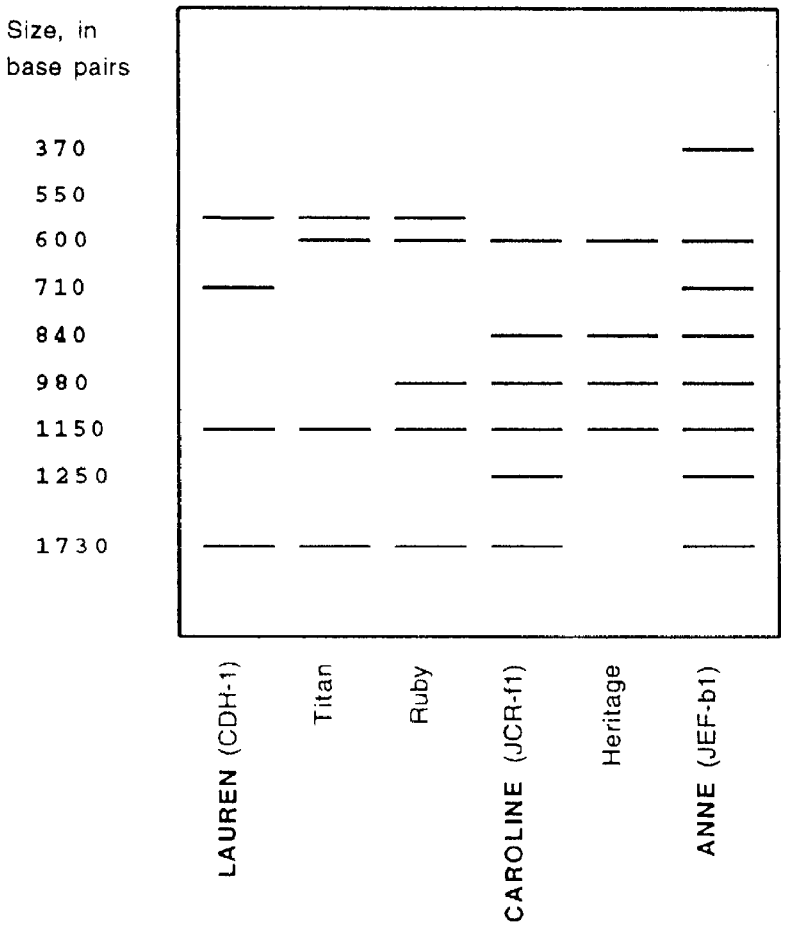

The FIG. 4 depicts the DNA fingerprints of CDH-1, 'Titan', and several other raspberry cultivars.

DESCRIPTION OF THE NEW CULTIVAR

The following is provided for a detailed description of the new cultivar for the purposes of intended use and identification. This cultivar is compared to the standard used in the area: 'Titan'. This description is a composite of information provided by cooperating scientists from plants grown in fields at Queenstown, Md., Cream Ridge, N.J., Blackstone, Va. and River Falls, Wis., from plant characteristics in the greenhouse at College Park, and from a survey of 25 evaluators.

Fruit Production

CDH-1 has been tested in a replicated planting in Cream Ridge, N.J., and in South central Pennsylvania.

TABLE 1

| CDH-1 yield and fruit weight | | |
|---|---|---|
| Yield in thousands of lbs/acre | NJ | 3.6 |
| Yield in thousands of lbs/acre | PA | 9.6 |
| Fniit Weight in grams | NJ | 4.2 |

Plant Characteristics

Figure 3:
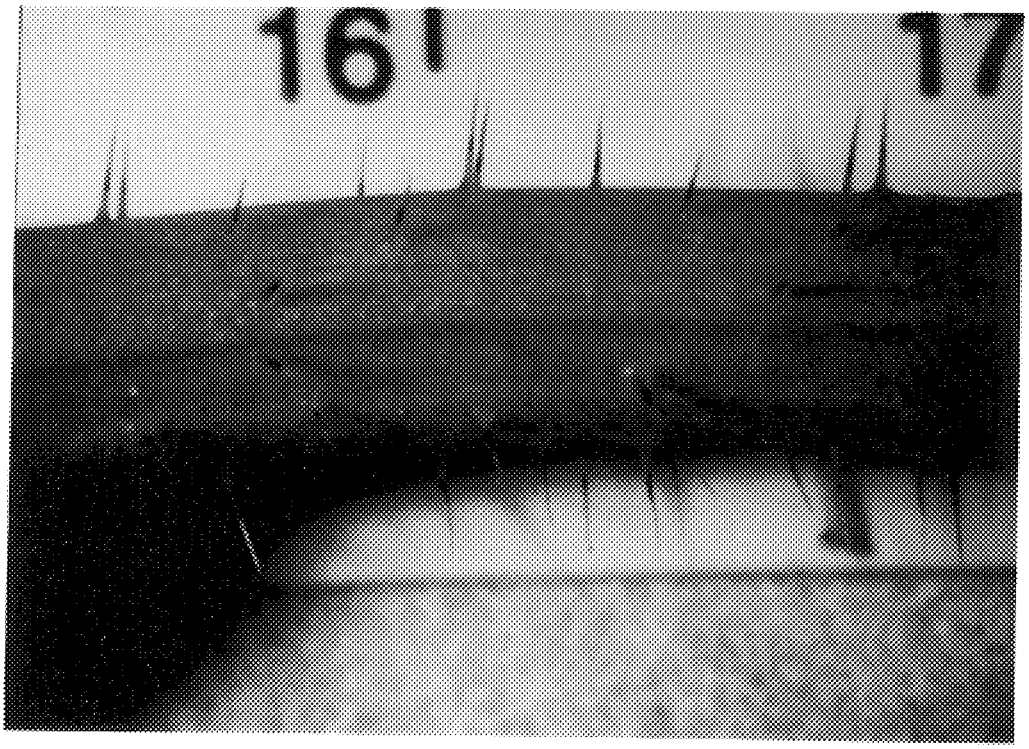
FIG. 3 shows the prickles of CDH-1.

CDH-1 produces a moderate amount of upright root suckers. The erect canes will branch occasionally and average 5 feet in height but range from 3 to over 7 feet in height depending on location. The plant form is more comparable to 'Titan' than 'Southland', which is shorter and has many more root suckers. Thorns are moderately dense (see FIG. 3). Primocane leaves are large and similar in presentation and serration to 'Titan'. Leaves are of The Royal Horticultural Society (RHS) color chart number 137B, trifoliolate, and pentafoliolate on vigorous primocanes. CDH-1 canes are cold hardy to −20° F. in the northern U.S., but will be killed by severe temperatures in early fall or late spring. This type of damage is often associated with *Phytophthora fragarae* root rot damage. CDH-1 almost never produces a fall crop on primocanes.

Figure 1:
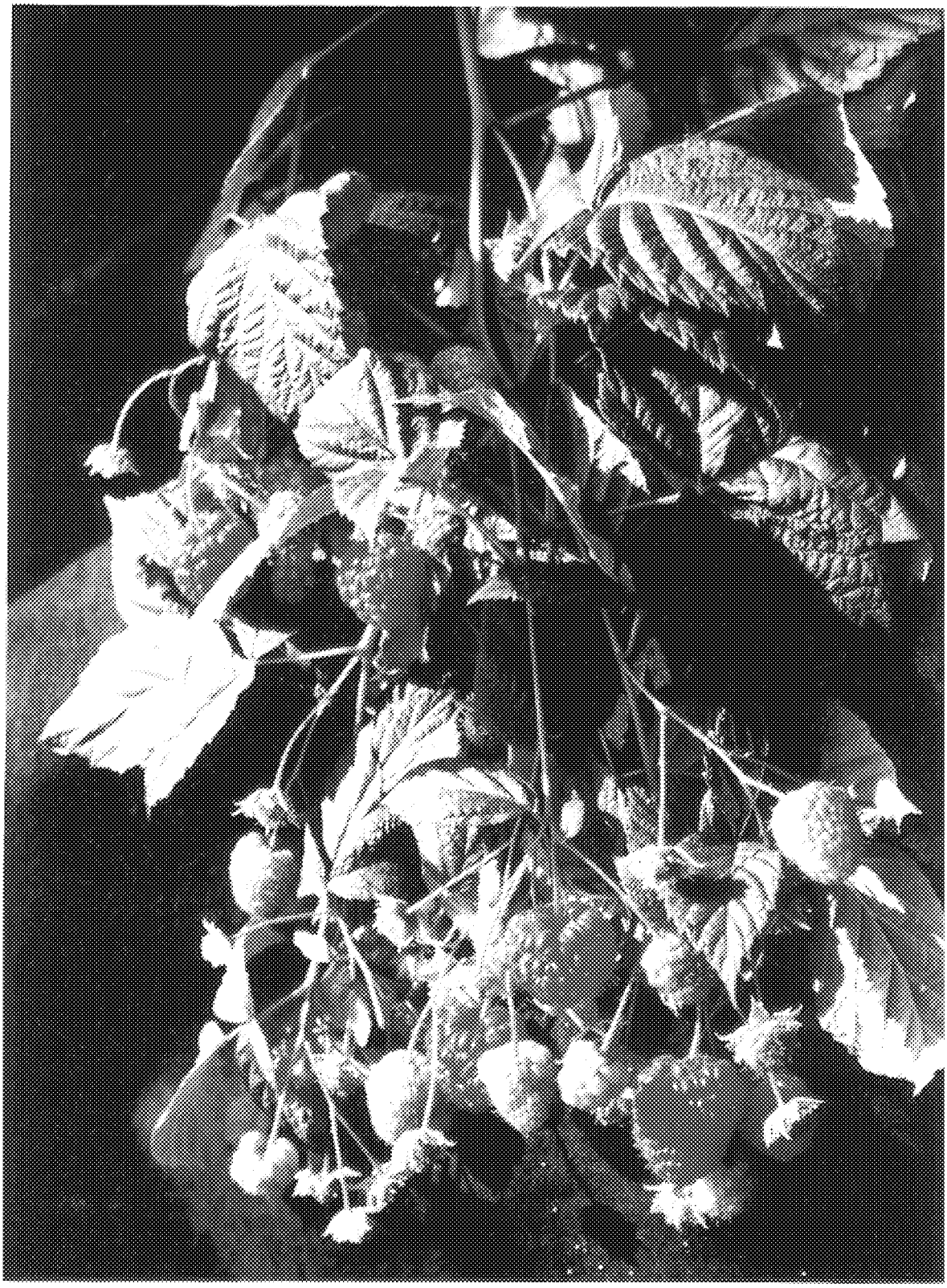
FIG. 1 shows a fruiting cluster of CDH-1, showing the exposure of the fruit.
Figure 2:
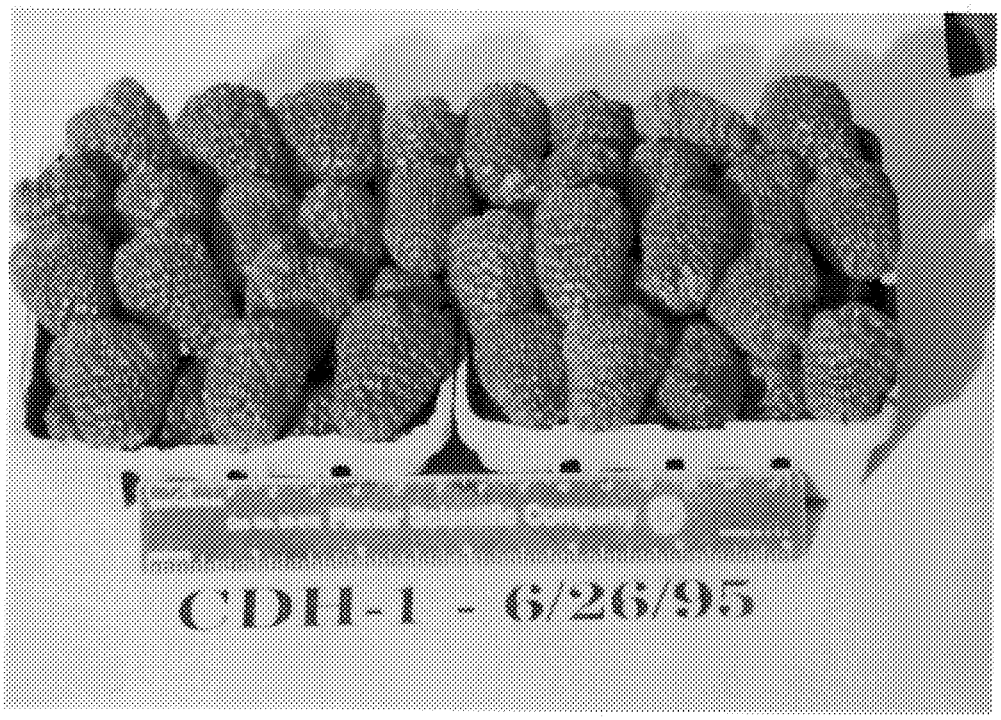
FIG. 2 shows the harvested fruit of CDH-1.

Fruit trusses are borne on the whole cane very early to mid-early in the spring cropping season. CDH-1 is high to moderately high yielding. Less than 5% of test sites showed low yields. Ninety-six percent of evaluators indicate fruit is cohesive, firm, or shippable. Fruit is large, moderately red, RHS color chart number 46B, truncated conic (see FIG. 2), symmetrical and readily separated from torus. The fruit is characterized by a slightly uneven collar and its size. In a Pennsylvania State University flavor panel, CDH-1 was the second most flavorful fruit of the 14 entrants. The plant is field tolerant to many diseases, including anthracnose, mildew and verticillium wilt; however, it is only moderately resistant to yellow rust. High mortality can be expected in fields heavily infested with *Phytophthora fragarae* although CDH-1 is more resistant to this organism than is 'Titan'. Fruit is relatively free of fungal pathogens until ripe. The plant is susceptible to cane borers.

Plant attitude at maturity is upright to slightly arching, requiring support with a full crop. Plants should be trellised on a 5–6 foot high, 2–4 wire trellis. Pruning and training is typical for a vigorous, shy suckering spring bearing cultivar. Bark is green through the season, turning brown in fall and exfoliating thereafter. Flowers are indistinguishable from other raspberry cultivars. Plants are self pollinating. Internode length is highly dependent on light and time of year; in the shade, lengths can exceed 2 inches, while in the late fall and in full sun, lengths are often less than one half inch. Cane density is moderate to low, close planting is suggested in warmer climates or the use of mulch is required to enhance root and root sucker growth, otherwise, the plants are very suited to single plant "hill" culture. This makes a relatively moderate canopy. Fruit are not adapted to mechanical harvest because their collar often closes over the recepticle. Although the fruit is easily removed, i.e. the drupelets abscise easily, sometimes it "hangs up" or remains on the plant. The fruit are firm and except when ripped during removal, are cohesive.

Leaflets range from 3–7 inches from base of petiole to apex of terminal leaflet blade. Primocane leaflet length is 8–18 cm. Terminal leaflet blade is 12.5 cm in length by 8.4 cm in width. Petiole length is 8.1 cm. Petiole diameter is 3.3 mm.

The measured weight of fruit in New Jersey in 1995 varied through the season and was measured from yields in June at 4.8 grams, through July at 3.0 grams, with an average weight of 4.2 grams for the season.

Nucleic Acid Fingerprinting

The unique DNA fingerprint of CDH-1 was produced by random amplified polymorphic DNA (RAPD) analysis. Leaf DNA's were isolated using a modified CTAB (hexadecyl trimethyl ammonium bromide) procedure (Rowland and Nguyen, 1993, *Biotechniques* 14: 735–736) without the final PEG precipitation step.

Amplification reactions were performed in volumes of 25 $\mu$l using a procedure described in Levi et. al., 1993, HortScience 28: 1188–1190). The reagents and conditions included 50 mM Tris HCL-pH 9.0, 20 mM NaCl, 4 mM $MgCl_2$, 1% Triton X-100, 0.1% Gelatin, 0.2 $\mu$M primer (Promega 80-34), 200 $\mu$M of each dNTPs, 0.028 units/$\mu$l of Taq DNA polymerase (Promega Corporation, Madison, Wis.) and 1 mg/ml of template DNA. The oligonucleotide primer was synthesized by Promega Inc, Madison, Wis.

DNA was amplified in a MJ programmable thermal control (Model PTC-100, MJ Research, Watertown, Mass.) programmed for 51 cycles of 40 sec at 94° C., 70 sec at 48° C., and 2 min at 72° C. Amplification products were analyzed by electrophoresis at 90 constant volts in 1.4% Sigma agarose gels with 0.5×TBE buffer. DNA bands were detected under UV light after staining with ethidium bromide and visualized by producing a negative image on a computer. Comparison of bands with a 123 base pair ladder indicate the presence of CDH-1 bands at 550, 710, 1150, and 1730 bp in primer 80-34. 'Titan' showed bands at 550, 600, 1150, and 1730 in primer 80-34. The existence of bands unique to either cultivar under the conditions of this test is proof of fundamental genetic differences between CDH-1 and 'Titan', the only other large fruited cultivar in the eastern U.S.

What is claimed is:

1. A new and distinct spring bearing red raspberry plant known as 'Lauren' as described herein, illustrated and identified by the characteristics set forth above.

* * * * *

DNA Bands for 'Lauren', 'Titan', 'Ruby', 'Caroline', 'Heritage', and 'Anne'